(12) United States Patent
Fischer

(10) Patent No.: US 11,044,997 B2
(45) Date of Patent: Jun. 29, 2021

(54) FITTING FOR SEATING FURNITURE AND SEATING FURNITURE COMPRISING SUCH A FITTING

(71) Applicant: BEHEERMAATSCHAPPIJ VERMEULEN BEESD B.V., Culemborg (NL)

(72) Inventor: Matthias Fischer, Bratislava (SK)

(73) Assignee: BEHEERMAATSCHAPPIJ VERMEULEN BEESD B.V., Culemborg (NL)

( * ) Notice: Subject to any disclaimer, the term of this patent is extended or adjusted under 35 U.S.C. 154(b) by 0 days.

(21) Appl. No.: 16/323,918

(22) PCT Filed: Jan. 13, 2017

(86) PCT No.: PCT/EP2017/050723
§ 371 (c)(1),
(2) Date: Feb. 7, 2019

(87) PCT Pub. No.: WO2018/033256
PCT Pub. Date: Feb. 22, 2018

(65) Prior Publication Data
US 2019/0159595 A1    May 30, 2019

(30) Foreign Application Priority Data
Aug. 16, 2016    (EP) .................................. 16184390

(51) Int. Cl.
*A47C 1/0355*    (2013.01)
*A47C 1/031*    (2006.01)
(Continued)

(52) U.S. Cl.
CPC ............ *A47C 1/0355* (2013.01); *A47C 1/031* (2013.01); *A47C 1/034* (2013.01); *A61G 5/1067* (2013.01); *A61G 5/14* (2013.01); *A47C 1/0342* (2013.01)

(58) Field of Classification Search
None
See application file for complete search history.

(56) References Cited

U.S. PATENT DOCUMENTS 4,506,925 A * 3/1985 Crum ...................... A47C 7/506
297/69
5,127,705 A * 7/1992 Antoine .................. A47C 1/035
297/68

(Continued)

FOREIGN PATENT DOCUMENTS

DE  20 2015 105 292 U1  11/2015
EP     2 084 992 A2      8/2009
(Continued)

OTHER PUBLICATIONS

International Search Report issued in Application No. PCT/EP2017/050723 dated Apr. 13, 2017 and English translation (5 pages).
(Continued)

*Primary Examiner* — David E Allred
(74) *Attorney, Agent, or Firm* — Flynn Thiel, P.C.

(57) ABSTRACT

A furniture fitting for an item of seating furniture. The furniture fitting has a base portion attaching to a furniture base that stands on a floor, a seat face portion attaching a seat face unit having a seat face, and a leg rest portion attaching a leg rest unit having a leg rest face. The seat face portion is attached to the base portion for movement between upper and lower terminal positions, and the leg rest portion is attached to the seat face portion for movement between a stowage terminal position and a use terminal position. The leg rest portion via a rear and a front pivot lever is attached (Continued)

to the seat face portion. A gear device kinematically couples the movement of the seat face portion in relation to the base portion to the movement of the leg rest portion in relation to the seat face portion.

25 Claims, 9 Drawing Sheets

(51) Int. Cl.
  *A47C 1/034* (2006.01)
  *A61G 5/10* (2006.01)
  *A61G 5/14* (2006.01)

(56) References Cited

U.S. PATENT DOCUMENTS

| | | | |
|---|---|---|---|
| 5,857,739 | A | 1/1999 | Smith |
| 6,227,489 | B1 | 5/2001 | Kitamoto et al. |
| 8,764,112 | B2 | 7/2014 | Fischer |
| 8,985,694 | B2 | 3/2015 | Fischer |
| 9,247,822 | B2 | 2/2016 | Fischer |
| 9,402,479 | B1 * | 8/2016 | Lin ............ A47C 1/0355 |
| 2004/0000803 | A1 * | 1/2004 | Guillot ............ A47C 3/03 297/270.1 |
| 2011/0043005 | A1 | 2/2011 | Fischer |
| 2012/0248831 | A1 | 10/2012 | Garland |
| 2013/0257110 | A1 | 10/2013 | Fischer |
| 2016/0270537 | A1 * | 9/2016 | Marshall ............ A47C 1/0355 |
| 2017/0071344 | A1 | 3/2017 | Marcantoni |
| 2017/0238711 | A1 | 8/2017 | Miller |

FOREIGN PATENT DOCUMENTS

| | | |
|---|---|---|
| EP | 2 609 834 A1 | 7/2013 |
| EP | 2 777 433 A1 | 9/2014 |
| EP | 2 801 293 A1 | 11/2014 |
| WO | 2018/033362 A1 | 2/2018 |

OTHER PUBLICATIONS

European Search Report issued in European Application No. 16184390.9 with English translation of category of cited documents corresponding to the present application dated Jan. 27, 2017 (8 pages).

* cited by examiner

FITTING FOR SEATING FURNITURE AND SEATING FURNITURE COMPRISING SUCH A FITTING

FIELD OF APPLICATION AND PRIOR ART

The invention relates to a furniture fitting for an item of seating furniture. Said furniture fitting serves for use in an item of seating furniture, in particular in the manner of a chair or sofa. According to the intended use, a furniture base, a seat face unit having a seat face, and a leg rest unit having a leg rest face are attached to such a furniture fitting of the generic type. The furniture fitting connects said components to one another and enables the mutual relative movement of said components. The invention furthermore relates also to an item of seating furniture having such a fitting.

In the case of such an item of seating furniture of the generic type and of a furniture fitting provided therefor it is provided that the seat face unit, on the one hand, and the leg rest unit, on the other hand, are repositionable in relation to the base unit. Proceeding from an initial state in which the leg rest unit is disposed below the seat face unit, the leg rest unit can thus be deployed toward the front so as to assume a use position. In a manner corresponding thereto, the seat face unit itself can be lowered, preferably be pivoted into a lowered position. The seat face is preferably lowerable only or largely in the rearward region.

An item of seating furniture of the generic type and a furniture fitting of the generic type can moreover have a back rest, or a corresponding fitting portion, respectively, this not being relevant in the context of the present invention.

In the case of a furniture fitting of the generic type, it is naturally desirable for said furniture fitting to be able to be produced in a cost-effective manner. However, many known seating furniture fittings which have a leg rest unit in multiple parts, dispose of a multiplicity of individual parts which hamper a cost-effective production and assembly. It is moreover desirable in the case of a furniture fitting of the generic type for said furniture fitting to be designed such that it is capable of use in a flexible manner, that is to say does not interfere excessively with the construction mode of the remaining part of the item of seating furniture. It is also desirable for the furniture fitting to be of a minor volume such that said furniture fitting, if possible, can be seen only upon closer inspection of the item of seating furniture.

Known seating furniture fittings are comparatively heavy and expensive. In particular, said known seating furniture fittings in terms of the construction height and construction width thereof can often only be disguised with difficulty, in particular when said known seating furniture fittings extend to a significant proportion into the upholstery, this requiring thick upholstery, on the one hand, and reducing the flexibility of the use of such fittings, on the other hand.

OBJECT AND ACHIEVEMENT

It is an object of the invention to make available a cost-effective furniture fitting which by virtue of a small installation size enables a particularly flexible use.

In order for said object to be achieved, a furniture fitting which has a base portion for attaching to a furniture base that stands on a floor, a seat face portion for attaching to a seat face unit having a seat face, and a leg rest portion for attaching a leg rest unit having a leg rest face is proposed.

The three portions mentioned, the base portion, the seat face portion, and the leg rest portion, by definition are inherently rigid components which by means of pivoting links and pivot levers yet to be explained hereunder are connected to one another, said pivoting links and pivot levers making available the attachment points for the respective units, the base unit, the seat face unit having the seat face, and the leg rest unit having the leg rest face of the item of seating furniture. Further portions of the respective same unit that are movable in relation to said above portions do not count as the base portion, the seat face portion, and the leg rest portion in the context of this invention. For example, in the case of a particular form of a leg rest unit, an additional portion which is movable on the leg rest portion could thus be provided, without per se being part of the leg rest portion of the fitting in the context of this invention. The mentioned fitting portions as well as the lugs and levers connecting said mentioned fitting portions, are preferably provided as metallic components.

The seat face portion is attached to the base portion so as to be movable between an upper and a lower terminal position. The leg rest portion is attached to the seat face portion so as to be movable between a stowage terminal position in which the leg rest portion is disposed below the seat face portion, and a use terminal position in which the leg rest portion is disposed in front of the seat face portion.

In the context of this invention, the terms "top" and "bottom" refer to a vertical furniture height direction (Z), the latter being defied by the alignment of the base fitting in the complete seating furniture. The terms "front" and "rear" refer to a furniture longitudinal direction (X) which corresponds to a straight-ahead viewing direction of a person sitting on the item of seating furniture. The direction that is orthogonal to the furniture height direction (Z) and the furniture longitudinal direction (X) is referred to as the furniture transverse direction (Y).

The seat face portion is lowerable between the upper and the lower terminal position thereof, wherein a rear part of the seat face portion is in particular lowered. This lowering capability is preferably between 2 and 7 cm.

The leg rest portion in the stowage terminal position thereof is disposed such that a leg rest unit attached thereto is disposed completely below a seat face unit that is attached to the seat face portion. When the leg rest portion is disposed in the stowage terminal position thereof, the leg rest unit is thus hidden, so to speak. The leg rest unit in the use terminal position of the leg rest portion is disposed in front of the seat face unit and is aligned so as to be approximately flush with the latter such that a person sitting on the seat face unit can comfortably place his/her legs on the leg rest unit. The repositioning of the leg rest portion is primarily a repositioning in the furniture longitudinal direction (X), in particular preferably by at least 40 cm or even at least 50 cm in the furniture longitudinal direction (X). Said repositioning of the leg rest portion is however preferably also associated with a tilting movement of the leg rest portion by 20 to 45°, so that the leg rest unit below the seat face unit can be aligned so as to significantly slope down toward the rear and in the use position can be aligned so as to be approximately horizontal.

The leg rest portion is attached to the seat face portion by means of a rear and a front pivot lever, wherein one of the pivot levers in relation to the seat face portion is movable in a pivotable manner about a first pivot axis that is locationally fixed in relation to the seat face portion and said pivot lever, and in relation to the leg rest portion is movable in a pivotable manner about a second pivot axis that is locationally fixed in relation to the leg rest portion and said pivot lever; and the other pivot lever in relation to the seat face portion is movable in a pivotable manner about a third pivot axis that is locationally fixed in relation to the seat face portion and said pivot lever, and in relation to the leg rest portion is movable in a pivotable manner about a fourth pivot axis that is locationally fixed in relation to the leg rest portion and said pivot lever.

A movement path of the leg rest portion in relation to the seat face portion is defined by the two pivot levers which in the furniture longitudinal direction are disposed behind one another. The four pivot axes, of which the first and the third pivot axis are attached to the seat face portion so as to be locationally fixed thereon and of which the second and the fourth pivot axis are attached to the leg rest portion so as to be locationally fixed thereon, when viewed in the direction of the furniture transverse direction form a quadrangle which further below will once again be discussed in order for the particularity of the invention to be explained. The spacings between the first and the second pivot axis and the third and the fourth pivot axis and/or the spacings between the second and the third pivot axis and the fourth and the first pivot axis are preferably dissimilar. In particular, the pivot axes of the front pivot lever can be mutually spaced apart farther than the pivot axes of the rear pivot lever, so as to implement the mentioned tilting movement of the leg rest portion.

A gear device for at least in phases kinematically coupling the movement of the seat face portion in relation to the base portion to the movement of the leg rest portion in relation to the seat face portion is provided.

Said gear device couples the movements of the seat face portion in relation to the base portion, as well as of the leg rest portion in relation to the seat face portion. This is desirable, on the one hand, since the lowering of the seat face portion is advantageous for achieving a comfortable seating position in the case of a deployed leg rest unit. Said coupling, on the other hand, has the effect that the weight force of the person sitting on the seat face is suitable for stabilizing in a seesaw manner the leg rest unit in the use position thereof.

However, it is considered advantageous in the context of the invention for the movements to not always be coupled or for there to be only a very weak coupling at least in phases, as will yet be explained further below.

Additionally to the coupling of the leg rest portion to the seat face portion by way of the gear device, the furniture fitting preferably has a drive installation by means of which a first of the pivot levers is driven for the purpose of transferring the leg rest portion to the use terminal position.

The drive installation, which is preferably designed so as to be very simple and comprises only one activation lever for manual activation, said activation lever being connected in a rotationally fixed manner to one of the pivot levers, in particular the front pivot lever, besides the weight force which can be coupled in by way of the seat face unit, offers a second drive possibility so as to transfer the leg rest unit to the use terminal position thereof, or to transfer the leg rest portion that is attached to the leg rest unit in the direction of the use position of said leg rest portion. On account thereof it becomes possible for a gearing in the gear device to be chosen which, proceeding from the stowage terminal position of the leg rest portion in the transfer in the direction of the use terminal position is associated initially with, if at all, only a very minor lowering of the seat face portion. The advantage of the latter will yet be explained further below.

The particularly simple design of the drive installation mentioned by way of an activation lever that is connected in a locationally fixed manner to one of the pivot levers does not represent the only possibility. Alternatively, the drive installation can comprise an activation element for manual activation, said activation element by way of a drive gear mechanism coupling in a drive torque into one of the pivot levers.

The purpose of such an additional drive gear mechanism between the activation element or the activation lever, respectively, on the one hand, and the pivot lever, on the other hand, instead of a direct linking mechanism lies in that a facilitated activation is possible in phases on account thereof. For this purpose, the drive gear mechanism is preferably configured so as to have a gearing ratio >1, wherein this particularly preferably is a variable gearing ratio. It is particularly advantageous for the drive gear mechanism to have a variable gearing ratio, wherein it is particularly advantageous when said ratio at the beginning of the deployment of the leg rest portion is more than 3:1 and in the case of the continuing transfer is at least in phases lower than 2:1.

The facilitated activation on account of the drive gear mechanism having a gearing ratio of more than 1 is particularly advantageous since the weight force acting on the seat face portion in the transfer of the leg rest portion from the stowage terminal position thereof to the use terminal position thereof at the beginning of the movement is preferably decoupled or almost decoupled from the movement of the leg rest portion. The movement of the leg rest portion in such a case at the beginning is thus introduced almost exclusively by way of the activation element and thus preferably manually. However, the latter can be excessively stiff when the gearing is dispensed with. Moreover, the leg rest portion in the stowage terminal position is secured by virtue of the spring force and optionally by virtue of an additional magnetic safeguard such that the gearing is advantageous also for overcoming said spring force and optional magnetic safeguard.

The variability of the gearing permits that the gearing ratio in this instance in the further course of the transfer of the leg rest portion to the use terminal position becomes lower such that the overall pivot angle of the activation element is not very much larger than the overall pivot angle of the driven pivot lever into which the drive torque is coupled.

One preferred design embodiment of such a drive gear mechanism provides that the activation lever is attached to the pivot lever by way of a lever link which is pivotable on a portion that is rotationally fixed to the activation lever and is pivotably connected to the pivot lever. This design having the lever link permits in a very simple manner for an initially very large gearing to be achieved. To this end, the linkage point of the lever link is to be disposed on the portion of the pivot lever such that said linkage point initially moves approximately but not completely orthogonally to the connection line between said linkage point and the second linkage point of the lever link on the pivot lever. A comparatively large pivoting movement of the activation lever therefore leads to only a minor pivoting movement of the pivot lever and thus to a large gearing. The angle ratios vary as the movement of the linkage point of the lever link on the pivot lever continues, such that the gearing is reduced.

An electrically driven variant in which the drive installation comprises an electric motor which couples a drive torque into one of the pivot levers is also possible. In the case of items of seating furniture having armrests, such an activation element that is linked by way of a gearing mechanism is to be considered such an armrest, or a portion of the latter, respectively.

The gear device preferably has a transmission characteristic according to which in the transfer of the leg rest portion from the stowage terminal position to the use terminal position in a movement phase, proceeding from the stowage terminal position, in which the first pivot lever travels 50% of the distance thereof between the stowage terminal position and the use terminal position of the leg rest portion, the seat face portion travels less than 50% of the distance thereof between the upper terminal position and the lower terminal position, and in a subsequent movement phase up to the use terminal position, in which the first pivot lever travels a further 50% of the distance thereof between the stowage terminal position and the use terminal position of the leg rest portion, the seat face portion travels more than 50% of the distance thereof between the upper terminal position and the lower terminal position.

This transmission characteristic means that the first half of the distance of the leg rest portion in the direction of the use terminal position is associated with a comparatively minor movement of the seat face portion. The latter travels less than 50% of the overall distance thereof in this first phase of the first half of the distance of the leg rest portion, wherein said less than 50% relate to the overall length of the path along which the seat face portion is movable between the upper and the lower terminal position of said seat face portion. The seat face portion preferably travels an even significantly lower proportion of the overall distance thereof, in particular less than 25%, particularly preferably less than 15% of said overall distance.

This means that, proceeding from the stowage position of the leg rest unit, the latter is deployed comparatively far in the direction of the use position of said leg rest unit, without the seat face in the meantime being lowered to a relevant extent. This decoupling, or only week coupling, of the movements leads to the weight force of the person sitting on the item of seating furniture in this first movement phase, the latter being manually initiated by way of the activation lever mentioned, for example, not yet playing any important part in the deployment of the leg rest unit. Accordingly, the deployment can be very tuned, and there is no risk of the leg rest unit painfully hitting the lower legs of the person sitting on the item of seating furniture. It is also associated with the transmission characteristic mentioned, that the weight force of the person sitting on the item of seating furniture toward the end of the movement, and thus when reaching the use terminal position of the leg rest portion, acts more intensely on the leg rest unit, or the leg rest portion, respectively, said leg rest unit in the use position therefore by way of the weight force of the person sitting on the item of seating furniture being very advantageously stabilized in terms of the position of said leg rest unit.

This characteristic is also of advantage for the procedure of returning the leg rest unit having the leg rest portion up to the stowage position. The retraction of the leg rest unit and thus the lifting also of the seat face unit and of the weight of the user is effected by way of the leg muscles, this being easy to the user in the case of stretched legs. As soon as the leg rest portion has been inwardly pivoted by 50% in the direction of the stowage terminal position of said leg rest portion, the major part (>50%) of the mechanical work for lifting the seat face unit has also already been performed such that subsequently there is no longer any strong tendency of the overall system to move back to the use position by virtue of the weight force of the person sitting on the item of seating furniture. In subjective terms, the item of seating furniture does not put up any resistance to the inward pivoting of the leg rest unit.

The gear device preferably has a transmission characteristic according to which in the transfer of the leg rest from the stowage terminal position to the use terminal position, in a movement phase proceeding from the stowage terminal position, in which the first pivot lever travels 33% of the distance thereof between the stowage terminal position and the use position of the leg rest portion, the seat face portion travels less than 10%, preferably less than 5%, of the distance thereof between the upper terminal position and the lower terminal position.

Hardly any movement, or no movement at all, respectively, of the seat face portion thus takes place in said first third of the movement of the pivot lever. In the inward pivoting of the leg rest portion in the direction of the stowage terminal position thereof, after approximately 70% of the pivot angle the kinetic energy of the leg rest unit therefore usually suffices for moving the leg rest portion further up to the terminal position thereof.

Only one front and one rear pivot lever are preferably provided in each case, wherein said pivot levers are in each case preferably narrower than 3 cm.

The use of in each case only one front and one rear lever is therefore advantageous since it is usually expedient in the case of an item of seating furniture according to the invention that the leg rest face by way of a gap-type interruption described further below offers a receptacle region for the pivot levers in the stowage terminal position. On account of the use of only one front and one rear pivot lever, said pivot levers in terms of the furniture transverse direction being disposed so as to be congruent, a narrow gap in the leg rest face suffices. The width of the pivot levers in that central portion in which said pivot levers according to the intended use are routed through the leg rest face is at maximum the 3 cm mentioned, preferably 2 cm or less. In the region of the axles by means of which the pivot levers are attached to the seat face portion, on the one hand, and to the leg rest portion, on the other hand, the pivot levers preferably dispose of pivot shafts that are fixedly connected to the pivot levers, said pivot shafts having a length of at least 5 cm, preferably at least 8 cm, but particularly preferably at maximum 15 cm, moments that arise on account of the non-centric impingement by force into the leg rest portion can be discharged into the seat face portion. Said pivot shafts can be configured as bar portions or tube portions which by way of a welded connection or screw connection are part of the pivot levers. A more cost-effective design is achievable when the pivot shafts are connected to the pivot levers by way of a forming process. The pivot lever can thus in particular be formed by two faces which bear on one another in the central portion and therein are connected by a screw connection, a soldered/braced connection, or a welded connection, said two faces however at the end side being bent in the manner of a fork, so as to on account thereof form a pivot shaft.

Alternatively to a design having in each case only one front and one rear pivot lever, designs in which said pivot levers are provided in tandem so as to be mutually spaced apart in the furniture transverse direction are also conceivable. It is however preferable herein for the spacing of the respective external faces of the pivot levers not to exceed 15 cm, so as to permit a hidden centric attachment of the furniture fitting. The use of in particular in each case two front and rear pivot levers permits a thinner design embodiment, for example with an extent of only 0.5 cm in the furniture transverse direction. In this case, two separate slot-type interruptions are preferably provided in the leg rest face.

The seat face portion is preferably linked to the base portion by means of at least one pivoting link, wherein two pivoting links having in each case dissimilar pivot axes are preferably provided to this end, as will yet be explained further below.

Furthermore, a drive link is preferably pivotably articulated on one of the pivot levers, preferably on the rear pivot lever, and the gear device is provided between the pivoting link and the drive link and disposes of a control track along which a guide element that is driven by the pivoting link is movable.

The at least one pivoting link which connects the base portion to the seat face portion and is attached so as to be pivotably movable on said base portion and said seat face portion, is accordingly preferably utilized to transmit the repositioning of the seat face portion that is caused by the weight force of the person seated to the leg rest portion. The use of a control track having a guide element that is movable along the control track herein permits the effect in the sense of the above-described non-linearity to be able to be designed in a flexible manner. Such a gear device having a control track in particular permits an initial mobility of the leg rest portion in relation to the base portion to be enabled in the case of a stationary seat face portion.

In the case of one preferred design embodiment the guide element is provided so as to be locationally fixed on the pivoting link and is engaged in the control track which in turn has a curved shaping. The guide track herein is preferably provided on the drive link and the latter is particularly preferably attached to the seat face unit by means of an intermediate link. This construction mode has been demonstrated as being particularly simple and is associated with very few movable components. The drive link that acts on one of the pivot levers is simultaneously the support for the control track and is attached to the seat face unit by way of an intermediate link. The guide element which is preferably provided so as to be locationally fixed on the pivoting link mentioned engages in the curved control track herein.

A design having a curved control track is not without alternatives. A linear control track is likewise possible, wherein a further intermediate link is preferably provided in this case, said intermediate link being pivotably attached to the pivoting link between the base portion and the seat face portion and being provided with the guide element.

The drive installation, that is to say in particular the activation lever for the manual activation, preferably acts on the pivot lever which is linked by means of the first and the second pivot axis and which preferably forms the front pivot lever.

This is in particular desirable in the case of a design in which in the stowage terminal position, a connecting line between the first pivot axis and the second pivot axis, conjointly with a connecting line between the second pivot axis and the fourth pivot axis, encloses an angle <20°, or the second pivot axis is even located in an over-dead-center position such that a quadrangle defined by the position of the first, second, third, and fourth pivot axis forms a concave quadrangle, the second pivot axis thereof forming the concave corner.

This design having a very stretched alignment of the two connecting lines mentioned, said design being defined by the alignment of one of the pivot levers and the leg rest portion, or even having an over-dead-center position of the second pivot axis, particularly preferably permits a comparatively large pivot angle, particularly preferably of at least 130°, of one of the pivot levers between the stowage terminal position and the use terminal position to be implemented, such that the direct connection of the seat face portion and of the leg rest portion by way of the pivot levers is enabled on account thereof. Were a smaller pivot angle to be pursued, while avoiding the stretched position mentioned, or the over-dead-center position mentioned, the pivot levers would have to be designed so as to be even longer so as to enable a sufficient deployment of the leg rest portion. However, in the case of most items of seating furniture, this is barely implementable by virtue of the installation space available and in particular by virtue of the limited height of the seat face above ground. This almost dead-center position, or even the over-dead-center position being possible, is also associated with the fact that the mentioned drive installation by means of which one of the pivot levers can in particular be manually pivoted is provided. The mechanical instability usually associated with approximating a dead-center position by virtue of the absence of the static certainty is overcome by way of directly driving one of the pivot levers.

In the case of a fitting according to the invention it is considered advantageous when the pivot axes of the pivot levers on the side of the seat portion, between the seat face portion and the leg rest portion, and/or of the pivoting links between the seat face portion and the base portion, are provided below the seat face of the seat face unit, preferably significantly therebelow, wherein this means at least 2 cm, preferably at least 4 cm. In terms of the seat face portion of the furniture fitting it is advantageous when the first and third pivot axis are provided below attachment points by means of which a base plate or a base frame of the seat face unit is connected to the seat face portion of the furniture fitting.

The pivot angle, which is swept by one of the pivot levers between the stowage terminal position and the use terminal position of the leg rest portion, is preferably at least 130°, particularly preferably at least 140°. The pivot angle, which is swept by the other pivot lever between the stowage terminal position and the use terminal position of the leg rest portion, is preferably at least 110°, particularly preferably at least 120°. The larger pivot angle is preferably swept by the front pivot lever.

Two pivoting links are preferably provided for the seat face portion to be movably attached to the base portion, wherein a first of the pivoting links is attached to the seat face portion so as to be pivotable about a fifth pivot axis that is locationally fixed in relation to the first pivoting link and the seat face portion, and is attached to the base portion so as to be pivotable about a sixth pivot axis that is locationally fixed in relation to the first pivoting link and the base portion; and a second of the pivoting links is attached to the seat face portion so as to be pivotable about a seventh pivot axis that deviates from the fifth pivot axis and is locationally fixed in relation to the second pivoting link and the seat face portion, and is attached to the base portion so as to be pivotable about an eighth pivot axis that deviates from the sixth pivot axis and is locationally fixed in relation to the second pivoting link and the base portion.

Two first pivoting links and two second pivoting links are preferably provided in each case herein, wherein the in each case two pivoting links in a furniture transverse direction are mutually spaced apart by not more than 15 cm. Like other components, said two pivoting links thus ensure that the overall width of the fitting, without taking into account any potential torsion rod for linking the drive installation, is hardly any larger than 15 cm. In the case of a design having two first pivoting links or two second pivoting links it is advantageous when the pivoting links of at least one of the pivoting link pairs are connected to one another, preferably by way of a connection in the region of one of the pivot axes of the pivoting links.

The linking of a seat face portion on the base portion by means of two pivoting links having in each case dissimilar pivot axes per se has already been implemented in the case of other items of furniture. In the case of the present furniture fitting the design in which in each case two first and two second pivoting links are provided in pairs is particularly preferable, said pivoting link pairs being in each case pivotable about the same pivot axes, wherein said pivoting link pairs by way of a spacing of at maximum 15 cm can be disposed so as to be centric below the seat face unit and thus to be barely visible from the outside, permitting such a design in particular also in the case of items of seating furniture without armrests.

The fifth and the seventh pivot axes are preferably mutually spaced apart by not more than 25 cm, particularly preferably by not more than 15 cm, and are preferably provided in a rearward region of the furniture fitting.

Providing the pivot axes of the pivoting links to be close to one another in such a manner permits said pivot axes to be attached at the far rear on the furniture fitting where comparatively much installation space is available. The attachment of pivoting links in a region further toward the front can thus be dispensed with such that the visibility of the furniture fitting from the outside is further minimized.

In order for the disposal of the pivoting links in the rear region of the furniture fitting to be implemented in particular, it is advantageous when the sixth and eighth pivot axis on the base portion side are disposed so as to be mutually offset in height, in particular to be mutually spaced apart by at least 4 cm in the furniture height direction.

The first and the second pivoting link connect the seat face portion and the base portion in a manner similar to how the above-described pivot levers connect the seat face portion and the leg rest portion to one another. Here too, dissimilar spacings between the pivot axes and thus also the dissimilar angles on the pivot axes are advantageous in order to achieve a tilting movement of the seat face portion. This tilting movement is ideally of such a manner that only a rearward end of the seat face unit is lowered while a forward-pointing end remains almost positionally stable such that the seat face portion is pivoted about a virtual pivot axis, so to speak.

In the case of a fully lowered seat face portion, and thus in the disposal of the leg rest portion in the use terminal position thereof, an imaginary connecting line between the pivot axes of one of the pivoting links, conjointly with the furniture longitudinal direction, encloses an angle <30°, preferably <20°. The respective pivoting link is thus aligned so as to be almost horizontal, this being advantageous with a view to a compact construction mode of the fitting. Both lugs are particularly preferably provided with such an alignment.

The furniture fitting preferably disposes of a spring installation by means of which the seat face portion and the leg rest portion are mutually impinged by a spring force.

The spring installation, on account of the attachment thereof to the leg rest portion, can be accommodated in a particularly elegant manner and does not have to be provided in the region on the seat face portion below the seat face unit which region is limited in terms of space. The spring, according to the intended use, is to approximately compensate the weight force of the leg rest such that the latter does not sink in a self-acting manner from the states thereof of maximum potential energy defined in the stowage terminal position and the use terminal position. Accordingly, the spring is preferably attached in such a manner that said spring in a transfer of the leg rest portion from the stowage terminal position to the use terminal portion is initially tensioned and then relaxed again. Accordingly, there exists a conversion position as of which the spring force of the tensioned spring no longer acts in the direction of the stowage terminal position but in the direction of the use terminal position.

The spring installation herein can in particular be configured as a spring installation having two articulation points which are mutually movable in a linear manner along a spring direction, wherein the spring direction lies in the direction of main extent of the leg rest unit, or conjointly with the latter encloses an angle of less than 20°. Said direction of main extent of the leg rest unit having the leg rest face which leg rest unit is to be attached to the leg rest portion is defined by the leg rest portion and the attachment locations for the leg rest unit that are provided on said leg rest portion.

The disposal described leads to the spring being able to be hidden so as to be almost invisible on the leg rest portion. The leg rest portion, corresponding to the leg rest unit which is to be supported by said leg rest portion, usually has a longitudinally extended shape by way of which the plane of main extent of the leg rest portion is defined. The spring extends approximately in said plane.

The disposal of the spring installation on the leg rest unit moreover also has the advantage that in the case of a series of furniture having dissimilar leg rests, dissimilar springs can be provided in pre-assembled units of the leg rest units, so as to depend on the respective weight of the leg rest. A heavier leg rest can thus be provided with a stronger spring installation.

The spring installation is preferably linked to dissimilar components of the furniture fitting at two articulation points. A first articulation point herein is provided on the leg rest portion, while a second articulation point is provided on one of the pivot levers or provided on a slide which is displaceable along a spring track and which by way of a spring lug is coupled to one of the pivot levers.

The use with a spring track having a slide disposed thereon is in particular advantageous since a purely linear movement of the second articulation point relative to the leg rest portion is achieved on account thereof, such that the spring is able to be accommodated in a very small installation space of the leg rest portion.

It can also be advantageous when the furniture fitting has a further spring assembly which comprises a spring which, in that state in which the leg rest portion has reached the use terminal position thereof, impinges the seat face portion with an upward or downward force. This can be a tension spring or a compression spring. Depending on the design embodiment, said spring in the lowered state of the seat face portion and thus in the case of the leg rest portion being disposed in the use terminal position, causes an impingement of the seat face portion with an upward or downward force and facilitates or hampers the return of the leg rest portion to the stowage terminal position.

The fitting can thus be adapted in a simple manner to people of different sizes by way of an appropriate design of said spring. This can be an adaption that is invariable when in operation, said adaption being performed, for example, only for the marketing of the fitting for different countries so as to correspond to the country-typical physiognomy. However, the spring assembly is preferably manually adjustable by the end user such that the force, by way of which the seat face portion when reaching the use terminal position of the leg rest portion is impinged by the spring, is adjustable. The end user can thus adapt the fitting to match his/her figure such that the leg rest portion when used remains in the position thereof in a stable manner until the user by way of slight pressure initiates the transfer to the stowage terminal position.

The invention furthermore relates to an item of seating furniture in the manner of a chair or a sofa, having a furniture fitting of the afore-described type.

Said item of seating furniture disposes of a base unit to which the base portion of the furniture fitting is attached. Said base unit can have at least one furniture foot piece for setting up the item of furniture, the base portion being attached so as to be locationally fixed on said furniture foot piece. Alternatively, the base unit can be configured as a rotatable base unit having at least one furniture foot piece for setting up the item of furniture, a rotary part being provided on said furniture foot piece so as to be rotatable about a vertical axis, the base portion of the furniture fitting in turn being attached so as to be locationally fixed on said rotary part.

The item of seating furniture furthermore disposes of a seat face unit which has a seat face of the item of seating furniture and which is attached to the seat face portion of the furniture fitting, as well as a leg rest unit which has a leg rest face and which is attached to the leg rest portion of the furniture fitting.

The seat face unit and/or the leg rest unit are/is preferably upholstered such as is mostly the case in sofas and chairs. In principle however, a furniture fitting according to the invention by way of the very compact installation size thereof also permits the use on items of seating furniture having only a thin upholstery or even on items of furniture having non-upholstered but otherwise compliant seat and back faces, such as are known, for example, as office furniture having compliant leather faces.

The leg rest portion of the furniture fitting in the case of an upholstered leg rest unit is preferably predominantly disposed within a space surrounded by the cover, wherein a drive horn can particularly preferably be provided on the lower side of the leg rest portion. Said drive horn preferably forms the lower termination of the leg rest portion. On account of a spacing of preferably at least 5 cm, particularly preferably of 7 cm, in relation to the leg rest face it is achieved that the weight force of the legs of the person sitting that is coupled into the leg rest unit can be positively discharged in the direction of the seating unit by way of the pivot lever that is articulated on the drive horn.

A design of the item of seating furniture in which the furniture fitting on the seat face unit is screw-fitted from below to a frame of the seat face unit is particularly preferable. For this purpose, the furniture fitting can have screw bores.

In the case of a design as a sofa, at least two fittings of the afore-described type by way of which the at least two seat face units and two leg rest units are repositionable in a mutually independent manner in relation to a common base unit are preferably provided.

In the case of a particular design, the leg rest face has at least one interruption which in relation to the use position of the leg rest unit points in the direction of the seat face unit, at least one of the pivot levers plunging into said interruption when the leg rest unit is located in the stowage position thereof.

A region of the leg rest face, in which the at least one interruption provided for receiving the at least one pivot lever is provided, is disposed herein so as to be centric in relation to a furniture transverse direction and herein has a width of at maximum 15 cm.

In order for the leg rest unit to be hidden in the stowage position thereof, it can be advantageous for a downwardly directed trim to be provided on the front end of the seat face unit, stowage space for at least a front portion of the leg rest unit being defined behind said trim. The linking of the leg rest unit to the seat face unit and the envisaged pivot angles of the pivot levers ensure that the leg rest unit in the transfer thereof from the use position to the stowage position passes a lowermost point and subsequently rises again. This permits a simple trim to be used so as to obscure the leg rest unit that disappears therebehind.

BRIEF DESCRIPTION OF THE DRAWINGS

Further advantages and aspects of the invention are derived from the claims and from the description hereunder of two preferred exemplary embodiments of the invention, the latter being described hereunder by means of the figures in which:

FIGS. 4A and 4B to 7A and 7B show the furniture fitting in a perspective view and a schematic lateral view in four states, proceeding from a state having a leg rest portion in a stowage terminal position, and ending in a state having the leg rest portion in a use terminal position;

DETAILED DESCRIPTION OF THE EXEMPLARY EMBODIMENTS

Figure 1:
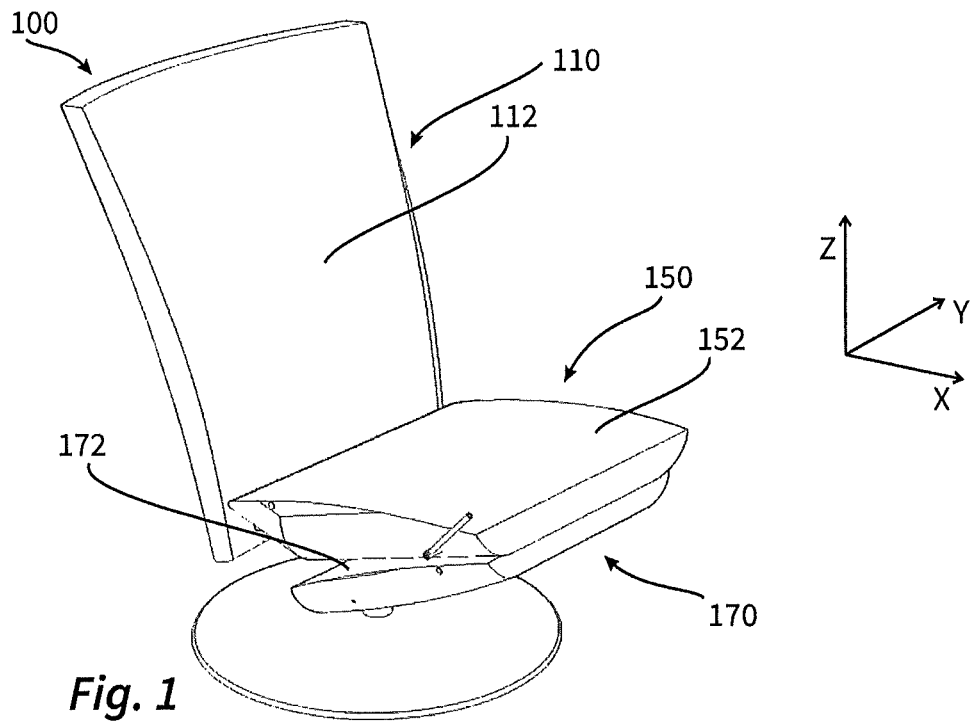
FIGS. 1 and 2 show an item of seating furniture in two states, specifically a state having the leg rest unit in the stowage position, and a state having the leg rest unit in the use position.
Figure 2:
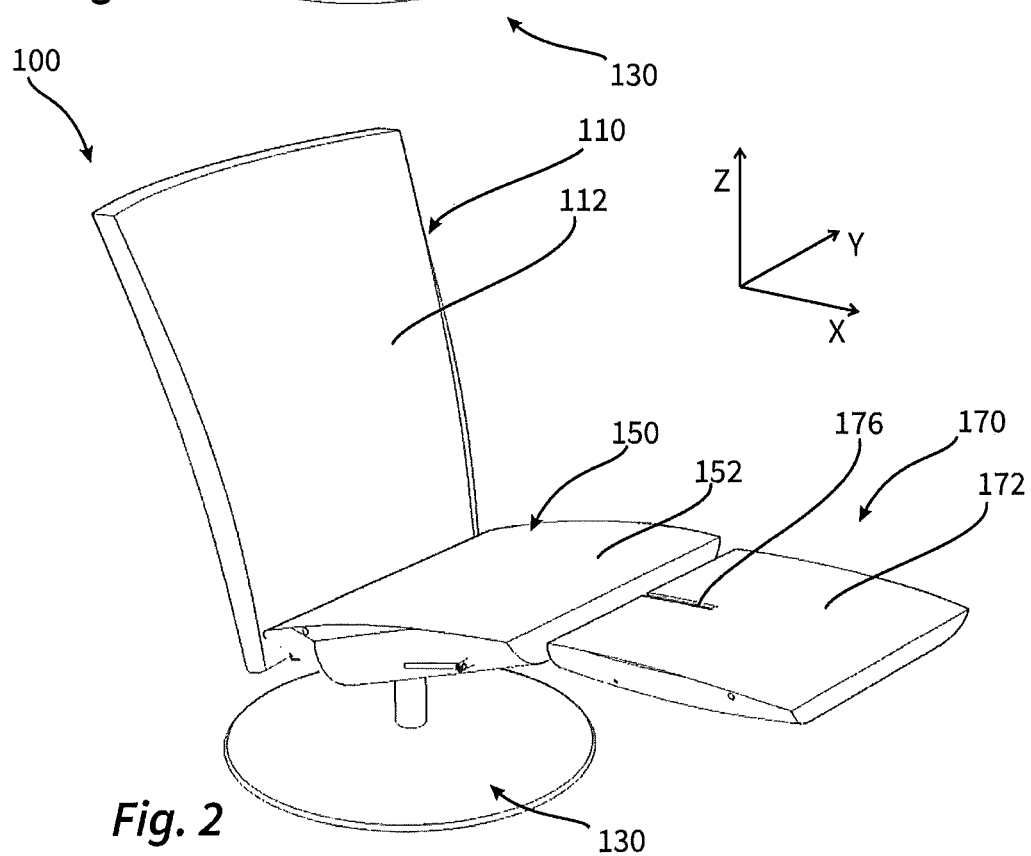

FIGS. 1 and 2 show an item of seating furniture 100 according to the invention in the form of a chair in two states. Said item of seating furniture 100 disposes of a base unit 130, a seat face unit 150 having a seat face 152, a leg rest unit 170 having a leg rest face 172, as well as a back rest unit 110 having a back rest face 112.

The seat face unit 150 in the state of FIG. 1 is located in an upper position in relation to the base unit 130 that is designed as a swivel foot. The leg rest unit 170 in the case of an upwardly directed leg rest face 172 is located in a stowage position below the seat face unit 150.

The seat face unit 150 in the state of FIG. 2 is lowered at the rear end and is thus located in the lower position thereof. The leg rest unit 170 is deployed such that said leg nest unit 170 in terms of the furniture longitudinal direction X is disposed in front of the seat face unit 150. The leg rest unit at the front is simultaneously pivoted downward by approximately 30° in relation to the alignment of said leg rest unit of FIG. 1.

Figure 3:
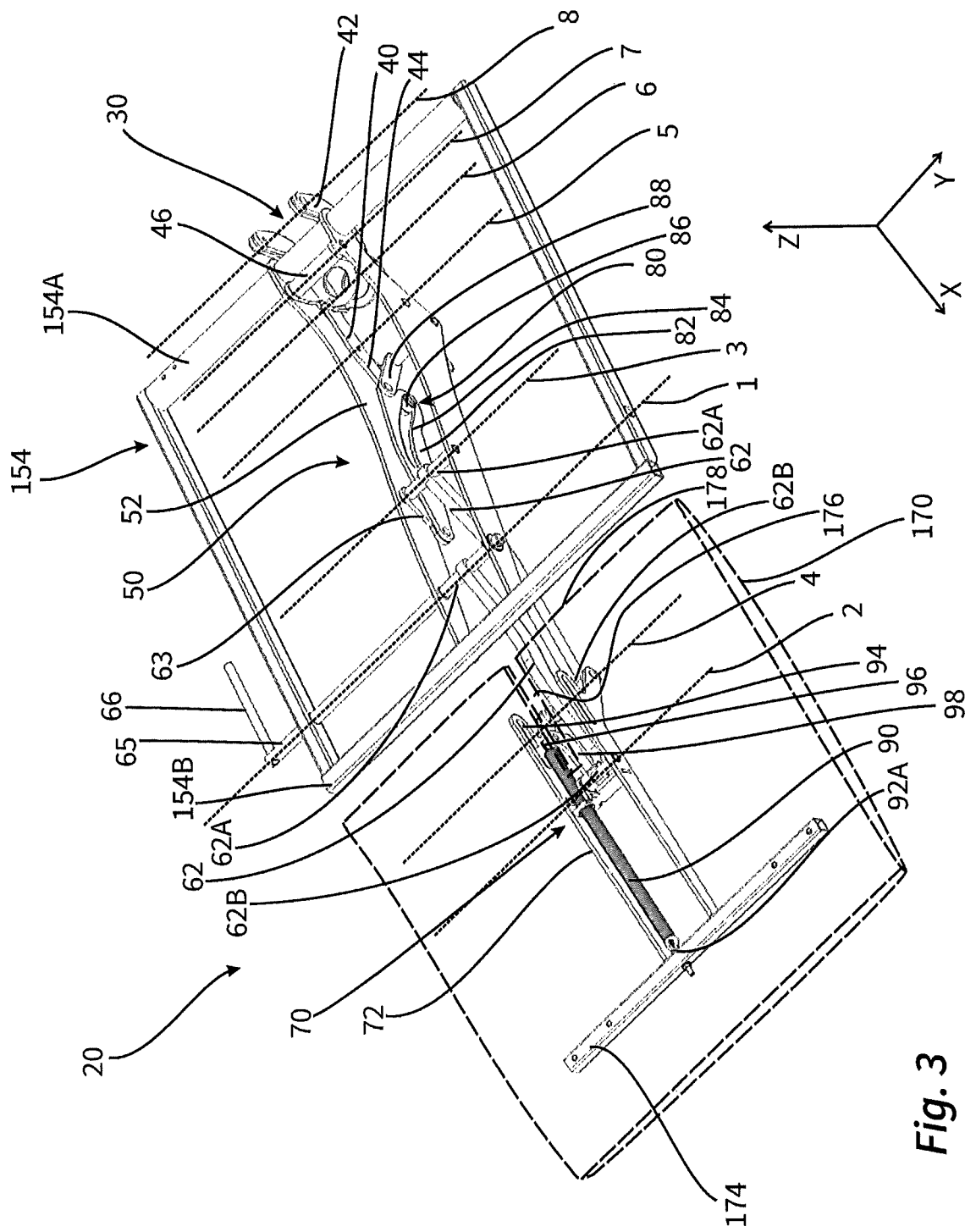
FIG. 3 shows a furniture fitting of the item of seating furniture which is responsible for the relative repositioning capability of a seat face unit and of the leg rest unit in relation to a base unit of the item of seating furniture.

The relative movement of the seat face unit 150 in relation to the base unit 130, as well as of the leg rest unit 170 in relation to the seat face unit 150, is implemented by way of a furniture fitting 20 which is illustrated in more detail in FIG. 3.

The furniture fitting 20 as main components has a base portion 30 which is attached to the base unit 130 that is configured as a swivel foot. Said furniture fitting 20 furthermore has a seat face portion 50 which is attached to a frame 154 of the seat face unit 150 and which disposes of two side plates 52 that are mutually spaced apart by just about 10 cm. The third main component of the furniture fitting 20 is the leg rest portion 70 which likewise disposes of two side plates 72 which are fastened to a transverse tube 174 at the end side of the leg rest unit.

The fundamental mutual relative mobility of said portions is implemented as follows. The seat face portion 50 is attached to the base portion 30 by means of two pivoting links 40, 42, wherein two first and two second pivoting links are in each case provided in parallel, said pivoting links hereunder however being in each case referred to collectively as the first, or the second pivoting link, respectively. The two rear pivoting links 42 are presently connected to one another by a welded connection tube 46 so as to achieve a higher stability here. Alternatively or additionally, this could also be implemented in a similar manner on the front pivoting link 40.

The first pivoting link 40 is articulated on the seat face portion 50 so as to be pivotable about the pivot axis 5 and articulated on the base portion 30 so as to be pivotable about the pivot axis 6. In a manner corresponding thereto, the second pivoting link 42 is articulated on the seat face portion 50 so as to be pivotable about the pivot axis 7 and articulated on the base portion 30 so as to be pivotable about the pivot axis 8. The pivoting links 40, 42 thus conjointly define the relative mobility of the seat face portion 50 in relation to the base portion 30, wherein the respective spacings between the axes are chosen such that in terms of the frame 154 the repositioning in relation to the base portion 30 takes place mostly in the region of the rearward tube 154A of said frame 154, while the front tube 154B in this movement remains so as to be almost locationally fixed in relation to the base portion 30.

In a manner similar to that by means of the pivoting links 40, 42, the leg rest portion 70 is also articulated on the seat face portion 50, wherein this is performed by means of two pivot levers 60, 62, wherein said pivot levers in the furniture longitudinal direction X are disposed behind one another. The pivot lever 60 forms the front pivot lever. The pivot lever 62 forms the rear pivot lever. Both pivot levers are provided on opposite ends with pivot shafts 60A, 60B, 62A, 62B which pivot shafts 60A, 60B, 62A, 62B are rotatably inserted between the side plates 52, 72 of the seat face portion 50 and of the leg rest portion 70. On account thereof, the first and the third pivot axis 1, 3 about which the pivot levers 60, 62 are pivotable in relation to the seat face portion 50, as well as the second and the fourth pivot axis 2, 4 about which the pivot levers 60, 62 are pivotably articulated on the leg rest portion 70 are defined. The pivot shafts 60A, 60B, 62A, 62B are presently configured as tubular portions that are welded to central regions of the pivot levers, but by way of a forming bending process or an offset can also be connected also in an integral manner to central regions that are configured as sheet-metal parts.

An activation lever 66 which by way of a torsion tube 65 is connected in a rotationally fixed manner to the front pivot lever 60 is provided for directly influencing the pivot angle of the first pivot lever 60 in relation to the seat face portion 50.

A gear device 80 for coupling the pivoting link 40 to the rear pivot lever 62 is furthermore provided. Said gear device 80 comprises an outrigger 44 which is fixedly attached to the first pivoting link 40, a guide element 86 being provided at the end of said outrigger 44. The gear device 80 furthermore disposes of a drive link 82 which is pivotably articulated on an outrigger 63 that is locationally fixed in relation to the pivot lever 62, said drive link 82 in turn being attached by way of an intermediate link 88 so as to be movable in relation to the seat face portion 50. A control track 84, within which the already described guide element 86 on the outrigger 44 of the pivoting link 40 engages, is provided in said drive link 82.

With a view to FIG. 3 it is to be furthermore explained that a spring installation 90 is provided on the leg rest portion 70. Said spring installation 90 is designed in the form of a coiled tension spring, the first articulation point 92A of the latter being provided directly on the leg rest portion 70. The second articulation 92B is provided on a spring slide 96 which is displaceable within a spring track 94 of the leg rest portion 70. The relative movement of the pivot levers 60, 62 in relation to the leg rest portion 70 is established in that a spring lug 98 that is pivotably movable acts between the pivot lever 60 and the spring slide 92 and is articulated on said pivot lever 60 and said spring slide 92.

The leg rest unit 170 is illustrated in dashed lines in FIG. 3. It can be seen that a central slot-type interruption 176 is provided on the rear end, said interruption 176 extending in the furniture longitudinal direction (X). Said interruption 176 serves for receiving the pivot levers 60, 62 in the case of the leg rest unit 170 being disposed in the stowage position.

The leg rest unit 170, in a manner not illustrated in more detail, disposes of a support plate which conjointly with an upholstery material is surrounded by a cover. Said cover is preferably open at the rear side 178 thereof, and is closable by means of a zip fastener or another mechanism. Said open side permits the cover together with the support plate and the upholstery material to be slid onto the leg rest portion 70 from the front. A form-fitting coupling to the leg rest portion 70 herein is preferably established in a tool-free manner by latch-fitting, or the like.

The functional mode of the furniture fitting 20 when deploying the leg rest portion 70 will be explained hereunder by means of FIGS. 4A to 7B.

Figure 4A:
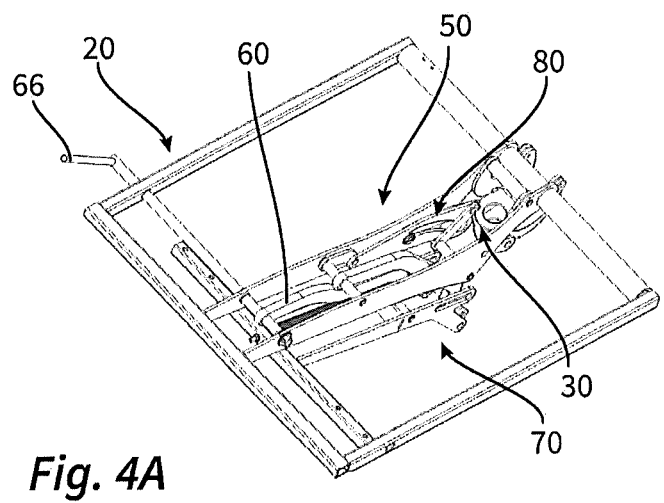
Figure 4B:
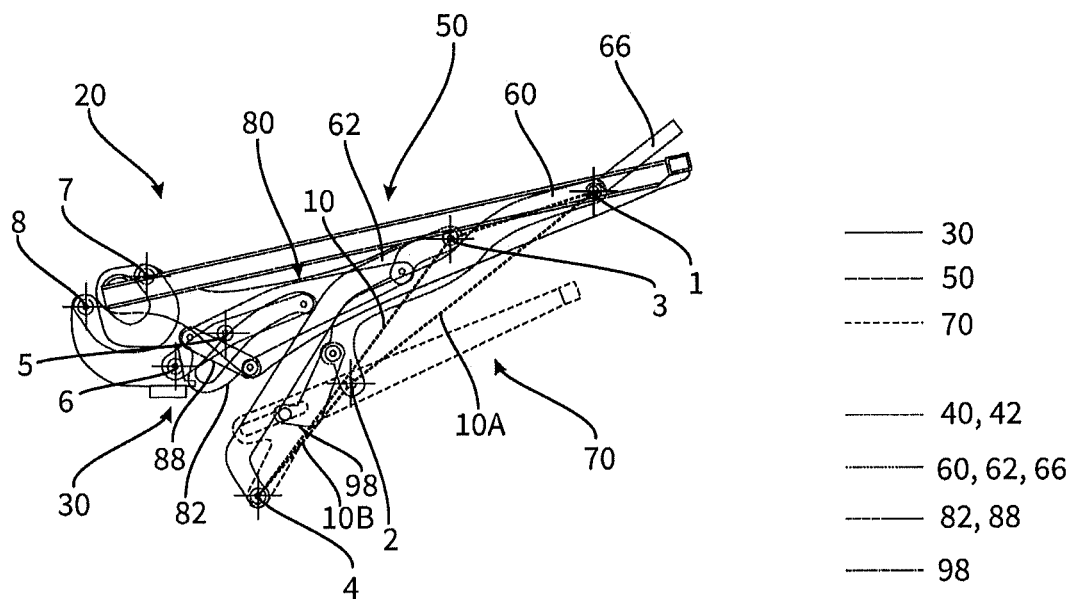

FIGS. 4A and 4B in a manner corresponding to FIG. 1 show an initial state in which the leg rest portion 70 is disposed below the seat face portion 50. A quadrangle 10 which is defined by the pivot axes 1, 2, 3, 4 is highlighted by the plotted line. As can be seen by means of FIG. 4B, said quadrangle in the initial state is in a so-called over-dead-center position and thus formed in the manner of a convex quadrangle. The second pivot axis 2 is thus disposed beyond a connecting line between the first and the third pivot axis 1, 3.

A weight force of the person sitting on the item of seating furniture that acts on the seat face unit 150 in this initial position thus does not yet have the effect that the leg rest portion 70 is impinged with a force in the direction of the use position of the latter, since the weight force indeed impinges the two pivoting links 40, 42 with moments in the clockwise manner in relation to FIG. 4B, but the guide element 86 at the end of the outrigger 44 of the pivoting link 42 by virtue of the alignment of the intermediate link 88 is not yet in the position of coupling a moment directed in the counterclockwise manner into the pivot levers 62, 60 of the leg rest portion 70.

In order for the transfer to be initiated, a manual coupling in of moments is required at the activation lever 66. On account thereof, as is shown in the transition from FIGS. 4A, 4B to FIGS. 5A, 5B, the two pivot levers 60, 62 are deflected in the counter-clockwise manner, wherein the over-dead-center position previously provided is also cancelled. This movement by virtue of the shaping of the control track 84 in the drive link 82 is initially not associated with the movement of the guide element 86, such that no pivoting of the pivoting links 40, 42 and no lowering of the seat face unit 150 takes place either.

Figure 5A:
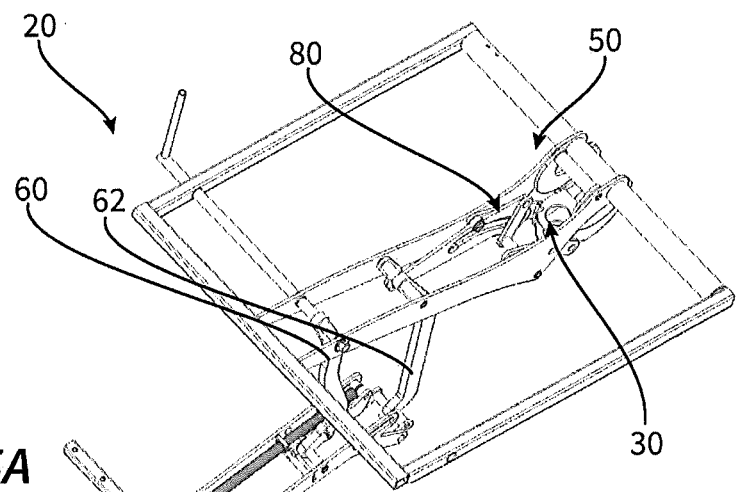
Figure 5B:
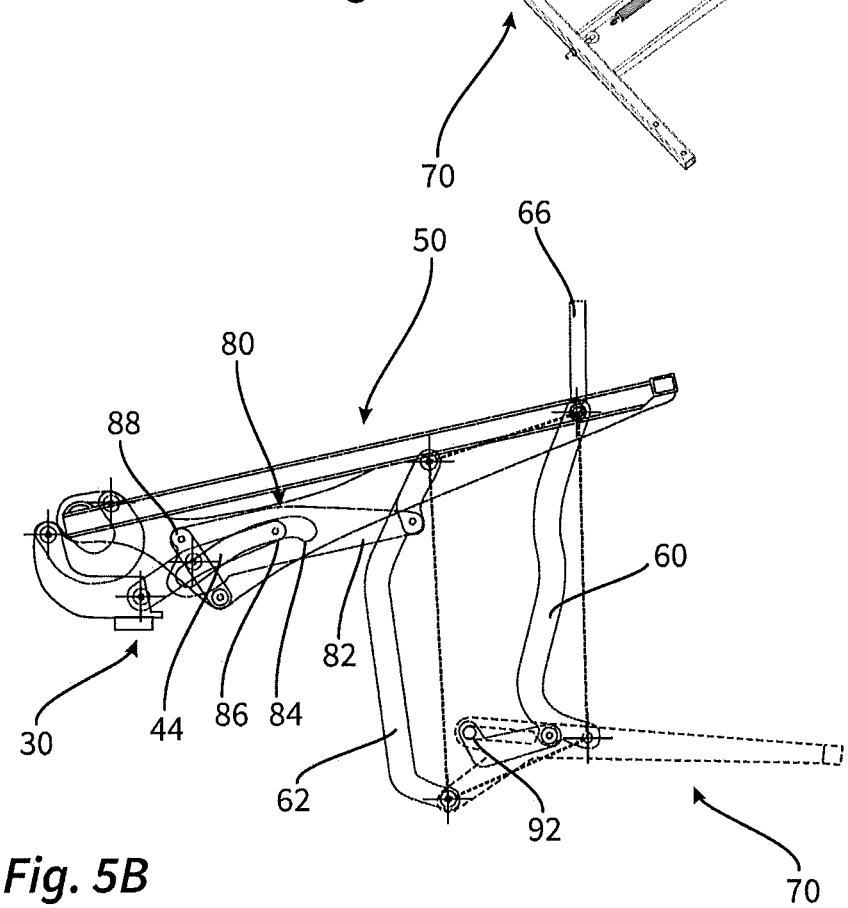
Figure 6A:
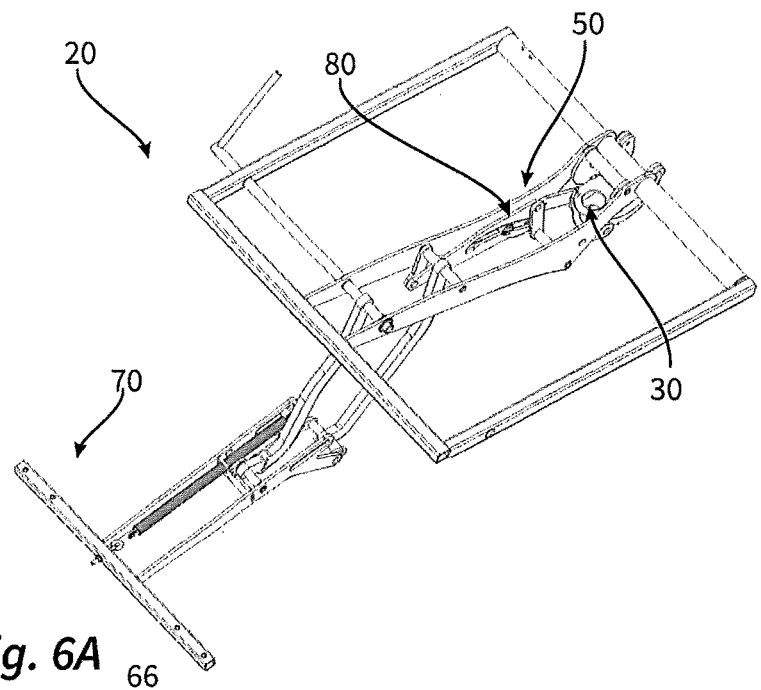
Figure 6B:
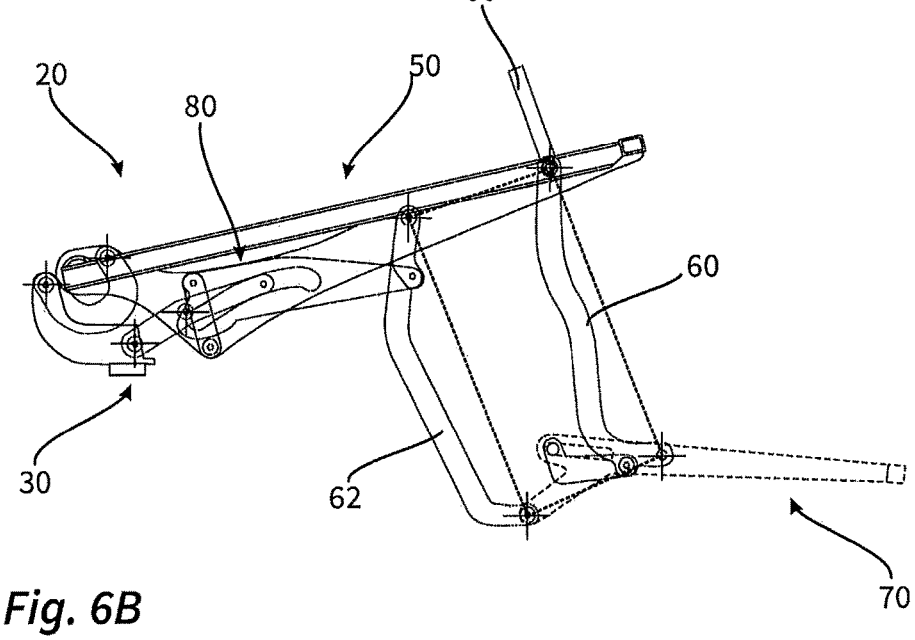

Only once the state of FIG. 5B has been approximately reached, the intermediate link 88 is pivoted sufficiently far so that the weight force of the person sitting on the item of seating furniture now begins to couple a torque that is directed in the counter-clockwise manner into the pivot levers 60, 62. A further manual impingement of the activation lever 66 can thus now cease. The leg rest portion 70, driven by the weight force of the person sitting on the item of seating furniture, is driven further in the direction of the use terminal position of said leg rest portion 70.

The state of FIGS. 5A and 5B is simultaneously also the conversion point in terms of the spring installation 90, that is to say the state of maximum tension in the spring installation 90. In the continuing movement in the direction of the state of FIGS. 7A, 7B the spring henceforth facilitates the further lifting of the leg rest unit 170 until the latter in the state of FIGS. 7A and 7B assumes the use position thereof. The gearing caused by the components of the gear device 80 in said use terminal position is at a maximum, that is to say that the weight force of the person sitting on the item of seating furniture in the state of FIGS. 7A, 7B stabilizes the position of the leg rest portion 70.

Figure 7A:
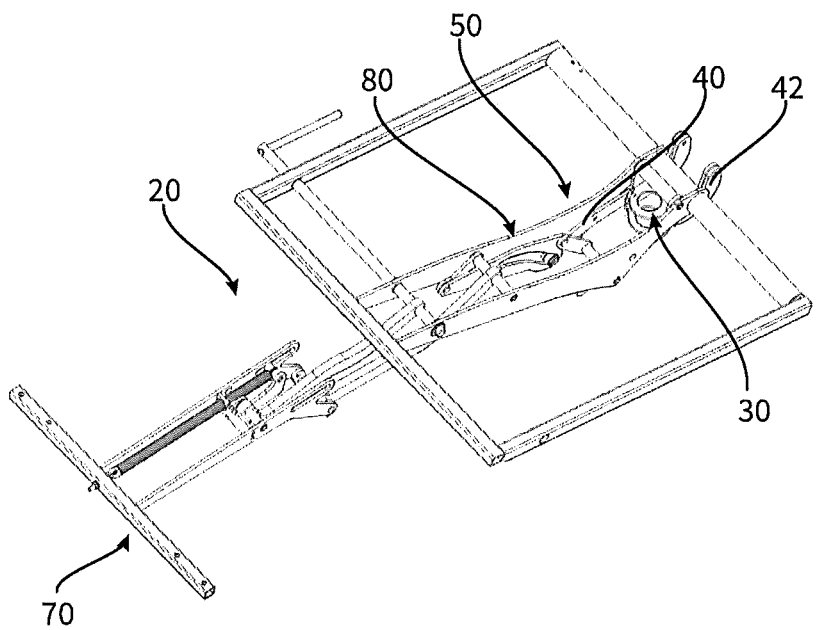
Figure 7B:
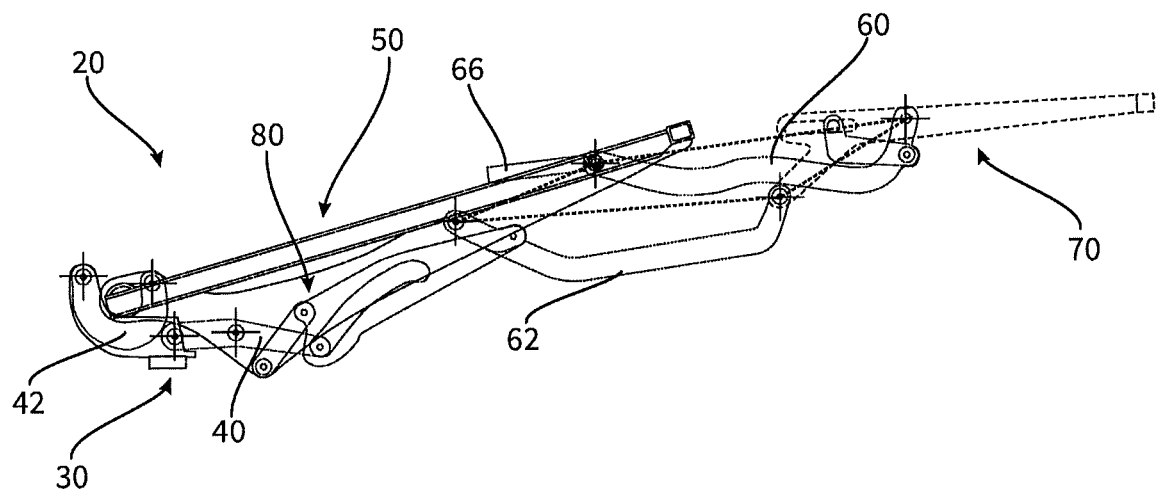

Proceeding from the state of FIGS. 7A, 7B, if a return to the initial state of FIGS. 4A and 4B is now desired, this is performed in that a moment directed in the clockwise manner is coupled into the leg rest portion 70 and thus into the pivot levers 60, 62 by the person seated, wherein the highest force in a haptically comfortable manner has to be applied at the beginning. From there, the continuing movement proceeds with increasing ease, this being owed to the transmission characteristic of the gear mechanism. As soon as the state of FIGS. 5A and 5B is again achieved in the return, the seat face unit 150 is in the upper terminal position thereof, such that the continuing movement up to the state of FIGS. 4A and 4B is caused solely by the spring force of the spring installation 90 and by the kinetic energy of the leg rest portion 70 that in the state of FIGS. 5A and 5B is present when folding in.

As can be readily seen by means of the figures, the furniture fitting 20 is extremely compact and, with the exception of the torsion tube 65 and the activation lever 66, is also completely disposed in a region in the center of the item of seating furniture that is at maximum only 15 cm wide. The furniture fitting 20 is therefore almost invisible on the item of seating furniture. This is also owed to the minor number of parts required. This in turn is also a result of the fact that the leg rest portion 70 and the seat face portion 50 are directly connected to one another by the two pivot levers 60, 62. Other furniture fittings here provide comparatively long chains of mutually movable elements which consequently are also more voluminous in terms of the construction.

Figure 8:
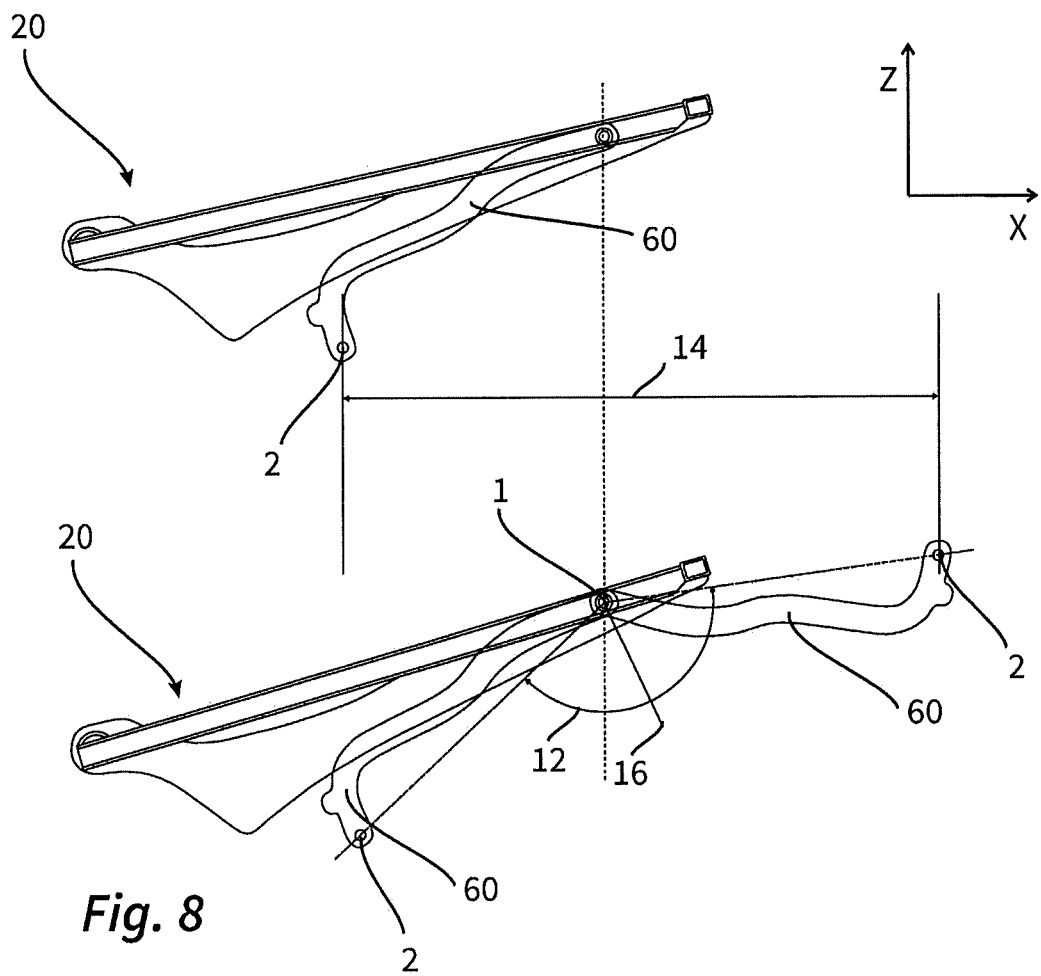
FIGS. 8 and 9 highlight the overall relative repositioning of a pivot lever relative to the seat face portion, and of the seat face portion relative to the base portion.
Figure 9:
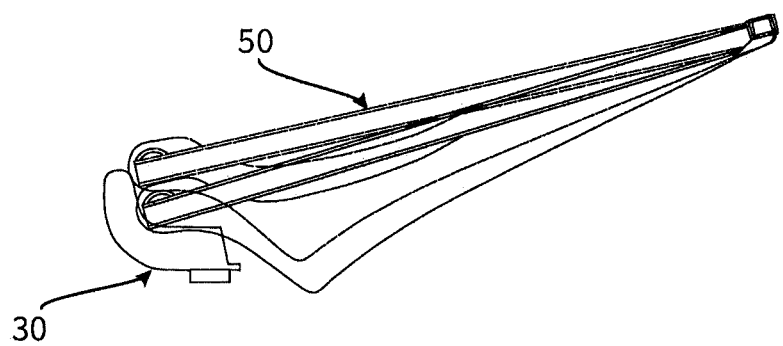

It can be seen by means of FIGS. 8 and 9 how large the movement of the first pivot lever is and how said pivot lever is coupled to the movement of the seat face portion.

As can be seen from FIG. 8, a far deployment path is enabled on account of the comparatively long pivot lever 60 and in particular on account of the fact that the front pivot lever is pivotable relative to the seat face portion by a pivot angle 12 of more than 140°. The second pivot axis in relation to the first pivot axis in the course of the transfer is presently repositioned by a distance 14 of more than 50 cm in the furniture longitudinal direction.

FIG. 9 highlights the movement of the seat face portion 50 relative to the base portion 30. The upper terminal position (illustrated in dashed lines) is assumed by the seat face portion 50 until the pivot lever 60 has almost reached the halfway position identified by the reference sign 16 in FIG. 8. The seat face portion 50 is lowered to the position illustrated in non-dashed lines in FIG. 9 only in the continuing movement of the pivot lever 60.

Figure 10A:
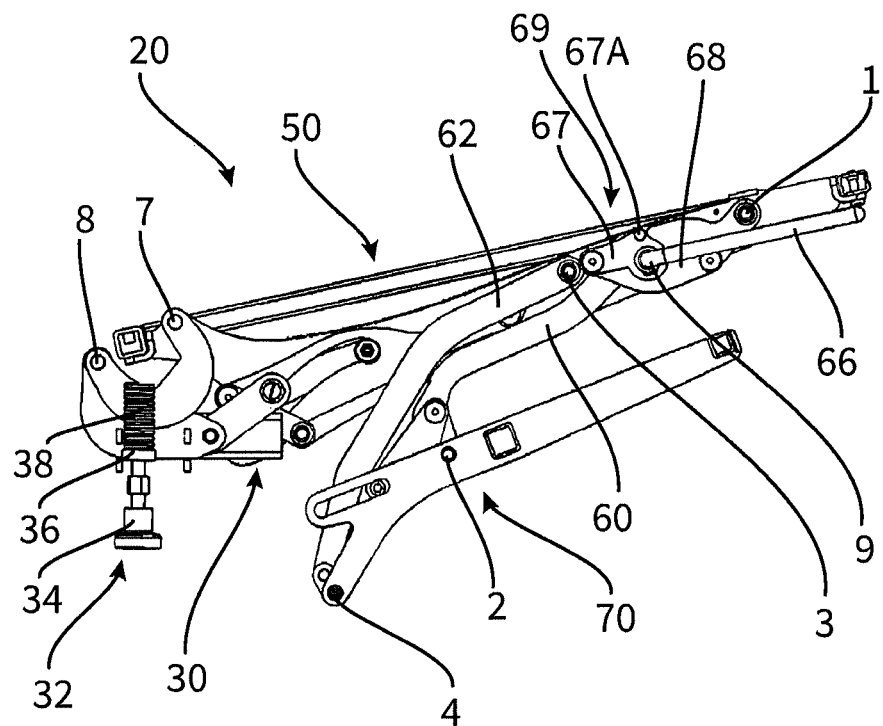
FIGS. 10A to 10D show a second exemplary embodiment which in terms of function has two relevant modifications in relation to the exemplary embodiment of FIGS. 1 to 9.
Figure 10B:
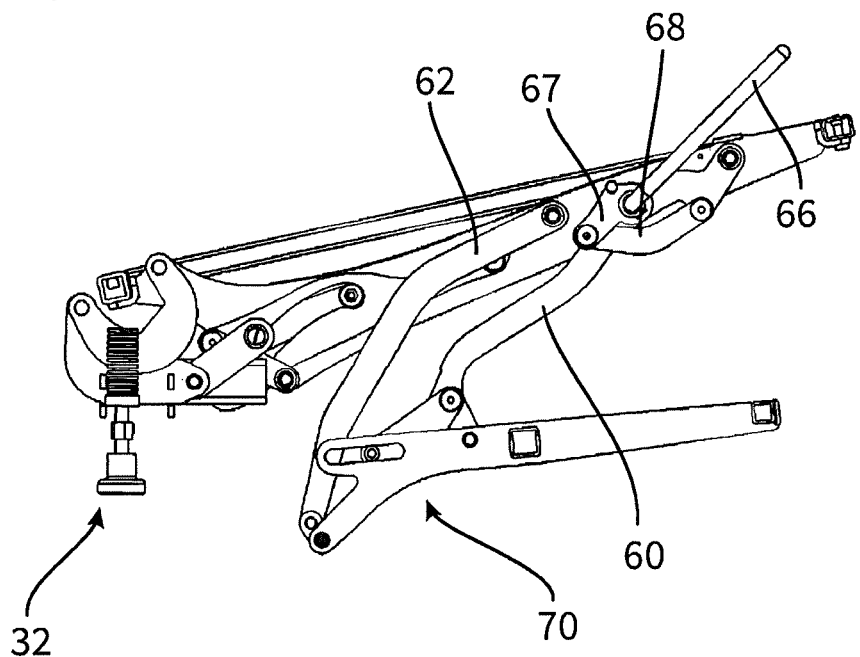
Figure 10C:
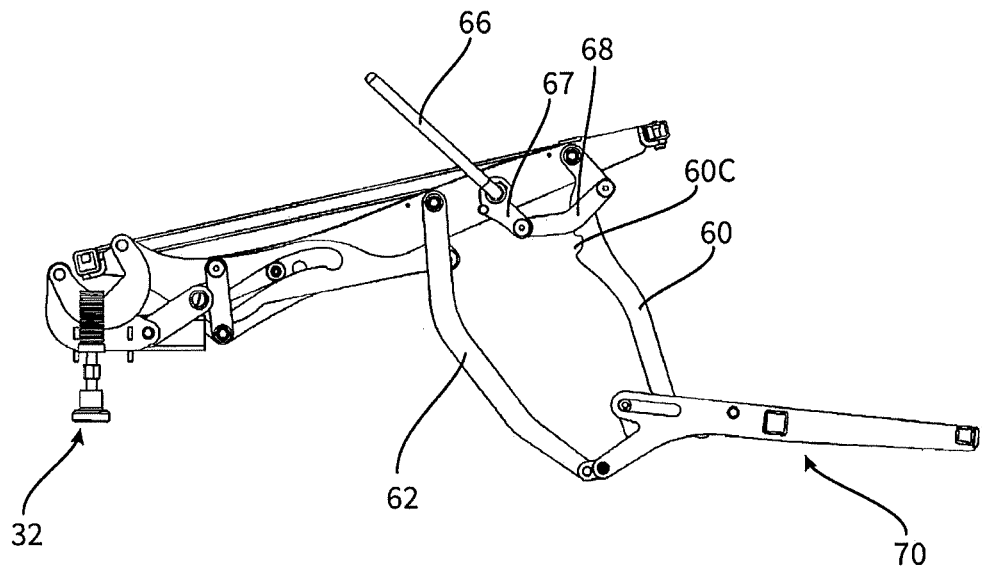
Figure 10D:
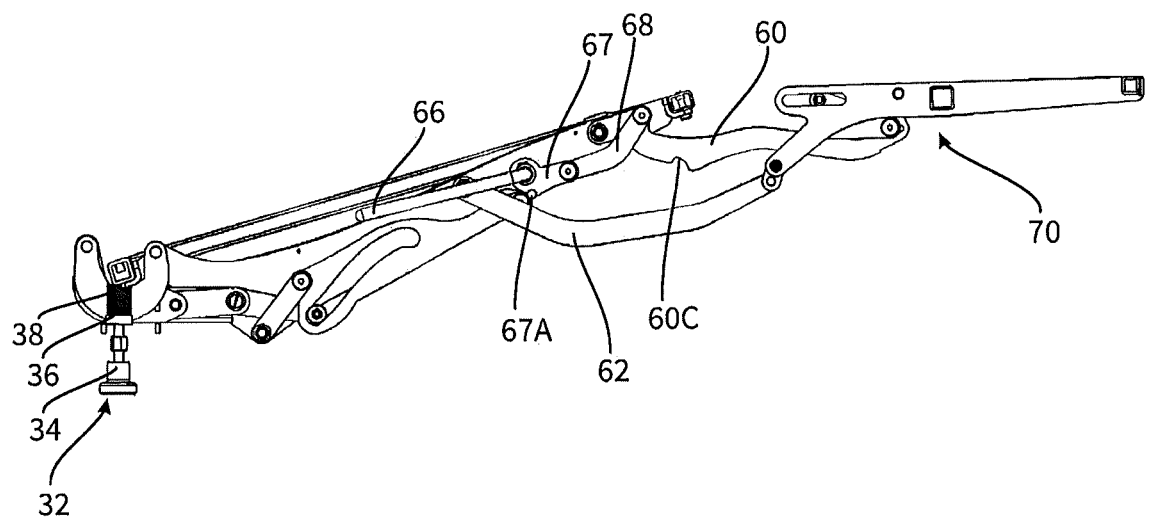

The exemplary embodiment of FIGS. 10A to 10D is largely similar to the preceding exemplary embodiment. All explanations above apply also to this second exemplary embodiment, with the exception of the points of differentiation explained hereunder. The figures show the deployment of the leg rest segment from the stowage terminal position (FIG. 10A) to the use terminal position (FIG. 10D).

The first substantial difference relates to the coupling of the activation lever 66 to the pivot lever 60. While a fixed connection exists here in the case of the above exemplary embodiment, a drive gear mechanism 69 intervenes in the case of the second exemplary embodiment. The activation lever 66, like the pivot lever 60, is pivotably attached to the seat face portion 50, however so as to be pivotable about a lever axis 9 that is spaced apart from the pivot axis 1 of the pivot lever 60.

The coupling of the activation lever 66 to the pivot lever 60 is performed by way of the drive gear mechanism 69 which disposes of a lever link 68 which, so as to be pivotable eccentrically in relation to the lever axis 9, is articulated on a portion 67 that is connected in a rotationally fixed manner to the activation lever 66. The opposite end of the lever link 68 is pivotably articulated on the pivot lever 60. As the transition from FIG. 10A to FIG. 10D shows, on account thereof it is likewise possible for a drive torque to be coupled into the pivot lever 60 by pivoting the activation lever 66.

The advantage in relation to the direct connection of the pivot lever 60 and the activation lever 66 according to the preceding exemplary embodiment lies in that the drive gear mechanism provides a variable gearing. At the beginning of the transfer, that is to say in the phase in which the weight force of the user offers hardly any contribution toward pivoting the leg rest portion 70, the initial gearing of approximately 10:1 of the activation lever 66 significantly facilitates the pivoting of the activation lever. This high gearing ratio is accomplished since the articulation point of the lever link 68 on the portion 67 lies almost level in height with the lever axis 9 and thus only a very minor repositioning of the lever link 68 takes place in the furniture longitudinal direction. However, since said repositioning of the lever link 68 that takes place in the furniture longitudinal direction is initially responsible for pivoting the pivot lever 60, in the case of a comparatively strong pivoting of the activation lever 66 only a minor pivoting of the pivot lever 60 results, said minor pivoting having a correspondingly higher moment. The leg rest portion 70 can thus be repositioned without great physical effort from the stowage terminal position in the direction of the use terminal position. The relative position of the linking point of the lever link 68 on the portion 67 relative to the lever axis 9 increasingly varies on account of the pivoting of the portion 67, such that the gearing is reduced down to the approximate range of 1:1.

In the case of the present exemplary embodiment yet a further particularity in the context of the drive gear mechanism 69 is implemented. A pin 67A that extends in the furniture transverse direction is attached to the portion 67 which is connected in a rotationally fixed manner to the activation lever 66. In a manner corresponding thereto, a lateral depression 60C is provided on the pivot lever 60. The pin 67A in the stowage terminal position of FIG. 10A bears on the flank of said depression 60C, said flank in FIG. 10C pointing downward. This has the effect that the force transmission to the pivot lever 60 is performed not only by way of the lever link 68 but also by way of the pin 67A and the flank of the depression 60C as the transfer of the leg rest portion 70 from the stowage terminal position in the direction of the use terminal position begins. This takes into account the fact that such a knuckle joint concept such as is implemented by the lever link 68 by virtue of production tolerances in the acute-angle position of FIG. 10A tends to be imprecise. It is therefore advantageous that the combination of the pin 67A and the depression 60C in this critical phase likewise enable the force transmission to the pivot lever 60.

The second substantial difference in relation to the first exemplary embodiment lies in the spring assembly 32. Said spring assembly 32 comprises a compression spring 38, the lower end of the latter bearing on a bearing face 36. Said bearing face 36 in turn, by means of a rotating handle 34 and of a thread (not illustrated in more detail), is attached to the base portion 30 so as to be height adjustable in relation to the latter.

As can be seen by means of FIGS. 10A to 10C, the spring assembly 32 during the transfer initially does not assume any function. A rear stay of the seat face portion 50 comes into contact with the upper end of the compression spring 38 only in the last moment before the use terminal position is reached, illustrated in FIG. 10D, said rear stay compressing said compression spring 38 until said compression spring 38 has the maximum compressed state as reached in the use terminal position.

The compression spring 38 then effects a force acting on the seat face portion, said force attempting to push the seat face portion upward and thus to again impinge the leg rest portion 70 with a force in the direction of the stowage terminal position. The pushing-down of the leg rest portion 70 for the purpose of returning the leg rest portion 70 to the stowage terminal position is thus facilitated.

The item of seating furniture can in this manner be adapted to the body proportions of a person. The shorter the legs of the user, the more difficult it is for the latter to initiate the return by way of the legs. This is facilitated by the assistance of the compression spring. The bearing face 36 can be lowered for persons with comparatively long legs, such that the effect of the compression spring 38 is minimized or even completely dispensed with.

The invention claimed is:

1. A furniture fitting for an item of seating furniture, comprising:
    a base portion for attaching to a base unit that stands on a floor;
    a seat face portion for attaching a seat face unit having a seat face; and
    a leg rest portion for attaching a leg rest unit having a leg rest face; and
    the seat face portion being attached to the base portion so as to be movable between an upper and a lower terminal position; and
    the leg rest portion being attached to the seat face portion so as to be movable between a stowage terminal position in which the leg rest portion is disposed below the seat face portion, and a use terminal position in which the leg rest portion is disposed in front of the seat face portion; and
    the leg rest portion being attached to the seat face portion by a rear and a front pivot lever;
    wherein a first one of the pivot levers in relation to the seat face portion is movable in a pivotable manner about a first pivot axis that is locationally fixed in relation to the seat face portion and said first one of the pivot levers, and in relation to the leg rest portion the first one of the pivot levers is movable in a pivotable manner about a second pivot axis that is locationally fixed in relation to the leg rest portion and said first one of the pivot levers; and
    wherein a second one of the pivot levers in relation to the seat face portion is movable in a pivotable manner about a third pivot axis that is locationally fixed in relation to the seat face portion and said second one of the pivot levers, and in relation to the leg rest portion the second one of the pivot levers is movable in a pivotable manner about a fourth pivot axis that is locationally fixed in relation to the leg rest portion and said second one of the pivot levers; and
    a coupling device for at least in phases kinematically coupling the movement of the seat face portion in relation to the base portion to the movement of the leg rest portion in relation to the seat face portion.

2. The furniture fitting as claimed in claim 1, further including:
    drive installation by which the first one of the pivot levers is driven for the purpose of transferring the leg rest portion to the use terminal position; and
    wherein the coupling device has a transmission characteristic according to which in the transfer of the leg rest portion from the stowage terminal position to the use terminal position:
        in a movement phase, proceeding from the stowage terminal position, in which the first one of the pivot levers travels 50% of the distance thereof between the stowage terminal position and the use terminal position of the leg rest portion, the seat face portion travels less than 50% of the distance thereof between the upper terminal position and the lower terminal position; and
        in a subsequent movement phase up to the use terminal position, in which the first pivot lever travels a further 50% of the distance thereof between the stowage terminal position and the use terminal position of the leg rest portion, the seat face portion travels more than 50% of the distance thereof between the upper terminal position and the lower terminal position.

3. The furniture fitting as claimed in claim 2, wherein:
    the coupling device has a transmission characteristic according to which in the transfer of the leg rest portion from the stowage terminal position to the use terminal position, in a movement phase proceeding from the stowage terminal position, in which the first pivot lever travels 30% of the distance thereof between the stowage terminal position and the use terminal position of the leg rest portion, the seat face portion travels less than 10% of the distance thereof between the upper terminal position and the lower terminal position.

4. The furniture fitting as claimed in claim 1, wherein:
the seat face portion is linked to the base portion by at least one pivoting link;
a drive link is pivotably articulated on one of the pivot levers; and
the coupling device is provided between the pivoting link and the drive link and comprises a control track along which a guide element that is driven by the pivoting link is movable.

5. The furniture fitting as claimed in claim 2, having one of the following features:
the drive installation comprises an activation lever for manual activation, said activation lever being connected in a rotationally fixed manner to one of the pivot levers; or
the drive installation comprises an electric motor which couples a drive torque into one of the pivot levers.

6. The furniture fitting as claimed in claim 2, having the following feature:
the drive installation comprises an activation element for manual activation, said activation element by way of a drive gear mechanism coupling a drive torque into one of the pivot levers.

7. The furniture fitting as claimed in claim 1, having the following features:
in the stowage terminal position, a connecting line between the first pivot axis and the second pivot axis, conjointly with a connecting line between the second pivot axis and the fourth pivot axis, encloses an angle >160°; and/or
in the stowage terminal position, the second pivot axis is located in an over-dead-center position such that a quadrangle defined by the position of the first, second, third, and fourth pivot axis forms a concave quadrangle, the second pivot axis thereof forming a concave corner.

8. The furniture fitting as claimed in claim 1, including the following feature:
a pivot angle, which in relation to the seat face portion is swept by one of the pivot levers between the stowage terminal position and the use terminal position of the leg rest portion, is at least 130°.

9. The furniture fitting as claimed in claim 1, including at least one of the following features:
the front pivot lever in relation to the seat face portion is movable in a pivotable manner about the first pivot axis, and in relation to the leg rest portion is movable in a pivotable manner about the second pivot axis;
a pivot angle of the front pivot lever, which is swept by the front pivot lever between the stowage terminal position and the use terminal position of the leg rest portion, is at least 130°;
an activation lever of a drive installation is connected in a rotationally fixed manner to the front pivot lever; and
a drive link is pivotably articulated on the rear pivot lever.

10. The furniture fitting as claimed in claim 1, wherein:
the base portion and the seat face portion are connected to one another by way of two pivoting links;
a first pivoting link of the two pivoting links being attached to the seat face portion so as to be pivotable about a fifth pivot axis that is locationally fixed in relation to the first pivoting link and the seat face portion, and is attached to the base portion so as to be pivotable about a sixth pivot axis that is locationally fixed in relation to the first pivoting link and the base portion; and
a second pivoting link of the two pivoting links being attached to the seat face portion so as to be pivotable about a seventh pivot axis that deviates from the fifth pivot axis and is locationally fixed in relation to the second pivoting link and the seat face portion, and is attached to the base portion so as to be pivotable about an eighth pivot axis that deviates from the sixth pivot axis and is locationally fixed in relation to the second pivoting link and the base portion.

11. The furniture fitting as claimed in claim 1, having the following features:
the furniture fitting comprises a spring installation by which the seat face portion and the leg rest portion are mutually impinged by a spring force; and
the spring installation is provided on the leg rest portion.

12. The furniture fitting as claimed in claim 11, wherein:
the leg rest portion defines a plane of main extent of the leg rest unit to be attached thereto; and
the spring installation has two articulation points which are mutually movable in a linear manner along a spring direction, wherein the spring direction lies in the plane of main extent of the leg rest portion, or conjointly with said plane of main extent encloses an angle of less than 20°.

13. The furniture fitting as claimed in claim 1, further including:
a spring assembly which comprises a spring which, in that state in which the leg rest portion has reached the use terminal position thereof, impinges the seat face portion with an upward or downward force.

14. The furniture fitting as claimed in claim 10, having at least one of the following features:
only one front and one rear pivot lever is in each case provided, wherein pivot shafts define the first, second, third, and fourth pivot axes;
at least two front pivot levers and/or at least two rear pivot levers are provided, wherein external ones of the pivot levers in a furniture transverse direction are in each case not mutually spaced apart by more than 15 cm;
two first pivoting links and two second pivoting links are in each case provided, wherein the two first pivoting links in a furniture transverse direction are not mutually spaced apart by more than 15 cm and the two second pivoting links in the furniture transverse direction are not mutually spaced apart by more than 15 cm;
the pivot levers are attached to the seat face portion and to the leg rest portion in such a manner and have a length in such a manner that the leg rest portion is pivoted between the stowage terminal position thereof and the use terminal position thereof between 20° and 45° in relation to the seat face portion, and/or the second pivot axis in relation to the first pivot axis in a furniture longitudinal direction is repositioned to the front by at least 40 cm;
the first and/or the third pivot axis in a furniture height direction are/is disposed below attachment points for attaching the seat face unit;
the fifth and/or the seventh pivot axis in the furniture height direction are/is disposed below attachment points for attaching the seat face unit;
at least one pivoting link in the disposal of the seat face portion in a lower terminal position thereof is aligned in such a manner that a connecting line between the pivot axes of said at least one pivoting link conjointly with the furniture longitudinal direction encloses an angle <30°;

the sixth and the eighth pivot axis are provided on the base portion at dissimilar heights in relation to the furniture height direction, and in the furniture height direction are preferably mutually spaced apart by at least 4 cm;

the furniture fitting comprises a back rest portion for attaching a back rest, wherein the back rest portion is preferably fixedly connected to the seat face portion, or by a coupling mechanism is connected to the base portion and the seat face portion in such a manner that said back rest portion, depending on the relative position of the seat face portion to the base portion, is repositioned in relation to both said seat face portion and said base portion;

the fourth pivot axis is provided on a downwardly protruding appendage of the leg rest portion.

15. An item of seating furniture in the manner of a chair or sofa, comprising:

at least one furniture fitting as claimed in claim 1;

the base unit to which the base portion of the furniture fitting is attached;

the seat face unit which has the seat face of the item of seating furniture and which is attached to the seat face portion of the furniture fitting; and the leg rest unit which has the leg rest face and which is attached to the leg rest portion of the furniture fitting.

16. The item of seating furniture as claimed in claim 15, wherein:

the leg rest face has at least one interruption which in relation to the use terminal position of the leg rest unit points in the direction of the seat face unit, at least one of the pivot levers plunging into said interruption when the leg rest unit is located in the stowage terminal position thereof.

17. The item of seating furniture as claimed in claim 15, having at least one of the following features:

the base unit has at least one furniture foot piece for setting up the item of seating furniture, the base portion of the furniture fitting being attached so as to be locationally fixed on said furniture foot piece;

the base unit is configured as a rotatable base unit having at least one furniture foot piece for setting up the item of seating furniture, a rotary part being provided on said furniture foot piece so as to be rotatable about a vertical axis, the base portion of the furniture fitting being attached so as to be locationally fixed on said rotary part or so as to be integral to the latter;

the item of seating furniture is configured as a chair; and the item of seating furniture is configured as a sofa, wherein the at least one furniture fitting comprises at least two furniture fittings at least two seat face units, including the seat face unit, and two leg rest units, including the leg rest unit, by way of said at least two furniture fittings being repositionable in a mutually independent manner in relation to a common base unit.

18. The item of seating furniture as claimed in claim 15, having at least one of the following features:

the first and/or the third pivot axis in the furniture height direction are/is disposed below the seat face;

fifth and/or seventh pivot axis in the furniture height direction are/is disposed below the seat face;

the seat face unit on a front end below the seat face comprises a trim, wherein a front edge of the leg rest unit in the stowage terminal position in relation to a furniture longitudinal direction is disposed behind said trim;

d. the leg rest unit comprises a cover which surrounds an upholstery and a support, wherein the cover at a rearward end thereof is open so as to be pushed onto the leg rest portion from the front; and the fourth pivot axis is provided on a downwardly protruding appendage of the leg rest portion, and is disposed at least 5 cm below the leg rest face.

19. The furniture fitting of claim 4, wherein:

the guide element is provided so as to be locationally fixed on the pivoting link; and the control track has a curved shaping.

20. The furniture fitting of claim 6, wherein:

the activation element is configured as a pivotable activation lever; and the activation lever is attached to the pivot lever by way of a lever link which is pivotable on a portion that is rotationally fixed to the activation lever and is pivotably connected to the pivot lever.

21. The furniture fitting of claim 8, wherein:

a pivot angle, which in relation to the seat face portion is swept by the other pivot lever between the stowage terminal position and the use terminal position of the leg rest portion, is at least 110°.

22. The furniture fitting of claim 10, wherein:

the fifth and the seventh pivot axes are mutually spaced apart by not more than 25 cm and are provided in a rearward region of the furniture fitting.

23. The furniture fitting of claim 12, wherein:

the spring installation is linked to dissimilar components of the furniture fitting at two articulation points;

a first articulation point of the two articulation points is provided on the leg rest portion;

a second articulation point of the two articulation points is provided on one of the pivot levers, or provided on one spring slide which is displaceable along a spring track and which by way of a spring lug is coupled to one of the pivot levers.

24. The furniture fitting of claim 13, wherein:

the spring assembly is manually adjustable such that the force, by way of which the seat face portion when reaching the use terminal position of the leg rest portion is impinged by the spring, is adjustable.

25. The item of seating furniture of claim 16, wherein:

a region of the leg rest face, in which the at least one interruption provided for receiving the at least one pivot lever is provided, is disposed so as to be centric in relation to a furniture transverse direction and has a width of at maximum 15 CM.

* * * * *